US007959951B2

(12) United States Patent
Stefano et al.

(10) Patent No.: US 7,959,951 B2
(45) Date of Patent: Jun. 14, 2011

(54) NITRIC OXIDE AND ITS BIOMEDICAL SIGNIFICANCE

(75) Inventors: George B. Stefano, Melville, NY (US); Wei Zhu, Old Westbury, NY (US); Kirk Mantione, Patchogue, NY (US)

(73) Assignee: The Research Foundation at State University of New York, Albany, NY (US)

( * ) Notice: Subject to any disclaimer, the term of this patent is extended or adjusted under 35 U.S.C. 154(b) by 459 days.

(21) Appl. No.: 10/526,091

(22) PCT Filed: Aug. 19, 2003

(86) PCT No.: PCT/US03/25966
§ 371 (c)(1),
(2), (4) Date: Aug. 15, 2008

(87) PCT Pub. No.: WO2004/037165
PCT Pub. Date: May 6, 2004

(65) Prior Publication Data
US 2006/0134233 A1    Jun. 22, 2006

Related U.S. Application Data

(60) Provisional application No. 60/405,787, filed on Aug. 23, 2002.

(51) Int. Cl.
*A61K 36/00* (2006.01)
*A61K 9/00* (2006.01)
*A61K 47/00* (2006.01)
(52) U.S. Cl. .......................... 424/725; 424/400; 424/439
(58) Field of Classification Search .................. None
See application file for complete search history.

(56) References Cited

U.S. PATENT DOCUMENTS

| 5,162,037 | A | 11/1992 | Whitson-Fischman |
| 6,200,594 | B1 | 3/2001 | Ernest et al. |
| 6,232,528 | B1 | 5/2001 | Scorza et al. |
| 6,254,899 | B1 | 7/2001 | Shrivastava |
| 6,417,349 | B1 * | 7/2002 | Kim et al. ............ 536/128 |
| 6,432,454 | B1 | 8/2002 | Shan et al. |
| 6,646,013 | B1 | 11/2003 | Barker et al. ............ 514/731 |

OTHER PUBLICATIONS

PDR for Herbal Medicine, First Edition, Salix Species, pp. 1111-1112, copyrighted 1998.*
The Healing Herbs, The Ultimate Guide to the Curative Power of nature's Medicines, White Willow, pp. 369-371, copyrighted 1991.*
Bilfinger et al., "Pharmacological Evidence for Anandamide Amidase in Human Cardiac and Vascular Tissues," International Journal of Cardiology, vol. 64, Suppl. 1, pp. S15-S22, 1998.
Bilfinger et al., "Human Aortocoronary Grafts and Nitric Oxide Release: Relationship to Pulsatile Pressure," Annals of Thoracic Surgery, vol. 69, pp. 480-485, 2000.
Deutsch et al., "Production and Physiological Actions of Anandamide in the Vasculature of the Rat Kidney," Journal of Clinical Investigation, vol. 100, No. 6, pp. 1538-1546, 1997.
Fimiani et al., "Opiate, Cannabinoid, and Eicosanoid Signaling Converges on Common Intracellular Pathways Nitric Oxide Coupling," Prostaglandins and Other Lipid Mediators, vol. 57, pp. 23-34, 1999.
Fimiani et al., "Morphine and Anandamide Stimulate Intracellular Calcium Transients in Human Arterial Endothelial Cells: Coupling to Nitric Oxide Release," Cellular Signaling, vol. 11, No. 3. pp. 189-193, 1999.
Magazine et al., "Morphine-Induced Conformational Changes in Human Monocytes, Granulocytes, and Endothelial Cells and in Invertebrate Immunocytes and Microglia are Mediated by Nitric Oxide[1]," Journal of Immunology, vol. 156, pp. 4845-4850, 1996.
Prevot et al., "Estradiol Coupling to Endothelial Nitric Oxide Stimulates Gonadotropin-Releasing Hormone Release from Rat Median Eminence Via a Membrane Receptor," Endocrinology, vol. 140, No. 2, pp. 652-659, 1999.
Prevot et al., "Morphine and Anandamide Coupling to Nitric Oxide Stimulates GnRH and CRF Release from Rat Median Eminence: Neurovascular Regulation," Brain Research, vol. 790, pp. 236-244, 1998.
Salzet et al., "Leech Immunocytes Contain Proopiomelanocortin: Nitric Oxide Mediates Hemolymph Proopiomelanocortin Processing[1]," Journal of Immunology, vol. 159, pp. 5400-5411, 1997.
Salzet et al., "Invertebrate Proenkephalin: δ Opioid Binding Sites in Leech Ganglia and Immunocytes," Brain Research, vol. 768, pp. 224-232, 1997.
Sonetti et al., "Microglia in Invertebrate Ganglia," Proc. Natl. Acad. Sci. USA, vol. 91, pp. 9180-9184, Sep. 1994.
Stefano, G. B., "Autoimmunovascular Regulation: Morphine and Anandamide Stimulated Nitric Oxide Release," Journal of Neuroimmunology, vol. 83, pp. 70-76, 1998.
Stefano et al., "Stimulatory Effects of Opioid Neuropeptides on Locomotory Activity and Conformational Changes in Invertebrate and Human Immunocytes: Evidence for a Subtype of δ Receptor," Proc. Natl. Acad. Sci. USA, vol. 86 pp. 6307-6311, Aug. 1989.
Stefano et al., "Presence of the μ3 Opiate Receptor in Endothelial Cells: Coupling to Nitric Oxide Production and Vasodilation," Journal of Biological Chemistry, vol. 270, No. 51, pp. 30290-30293, 1995.
Stefano et al., "Evidence for the Involvement of Opioid Neuropeptides in the Adherence and Migration of Immunocompetent Invertebrate Hemocytes," Proc. Natl. Acad. Sci. USA, vol. 86, pp. 626-630, Jan. 1989.
Stefano et al., "Cannabinoid Receptors are Coupled to Nitric Oxide Release in Invertebrate Immunocytes, Microglia, and Human Monocytes," Journal of Biological Chemistry, vol. 271, No. 32, pp. 19238-19242, 1996.
Stefano et al., "[D-Ala$^2$]Deltorphin I Binding and Pharmacological Evidence for a Special Subtype of δ Opioid Receptor on Human and Invertebrate Immune Cells," Proc. Natl. Acad. Sci. USA, vol. 89, pp. 9316-9320, Oct. 1992.

(Continued)

*Primary Examiner* — Christopher R Tate
*Assistant Examiner* — Randall Winston
(74) *Attorney, Agent, or Firm* — David E. Rook; Hoffman Warnick LLC (57) ABSTRACT

The invention relates to nitric oxide (NO) stimulating extracts from various plants. Such extracts contain compounds known as healthin I and healthin II. Specifically, the invention provides partially purified plant extracts that have NO stimulating activity, methods of isolating and partially purifying such extracts from plant materials. In addition, the invention provides methods and materials for treating diseases and conditions that require modification of cellular levels of NO, for example, diseases and conditions involving inflammation.

13 Claims, 7 Drawing Sheets

OTHER PUBLICATIONS

Stefano et al., "*Mytilus edulis* Hemolymph Contains Pro-Opiomelanocortin: LPS and Morphine Stimulate Differential Processing," Molecular Brain Research, vol. 63, pp. 340-350, 1999.

Stefano et al., "Enkelytin and Opioid Peptide Association in Invertebrates and Vertebrates: Immune Activation and Pain," Immunology Today, vol. 19, No. 6, pp. 265-268, Jun. 1998.

Stefano et al., "Morphine- and Anandamide-Stimulated Nitric Oxide Production Inhibits Presynaptic Dopamine Release," Brain Research, vol. 763, pp. 63-68, 1997.

Stefano et al., "Invertebrate Opioid Precursors: Evolutionary Conservation and the Significance of Enzymatic Processing," International Reviews Cytol., vol. 187, pp. 261-186, 1999.

Stefano et al., "Long-Term Exposure of Human Blood Vessels to HIV gp120, Morphine, and Anandamide Increases Endothelial Adhesion of Monocytes: Uncoupling of Nitric Oxide Release," Journal of Cardiovascular Pharmacology, vol. 31, pp. 862-868, 1998.

Stefano et al., "Antagonism of LPS and IFN-γ Induction of iNOS in Human Saphenous Vein Endothelium by Morphine and Anandamide by Nitric Oxide Inhibition of Adenylate Cyclase," Journal of Cardiovascular Pharmacology, vol. 31, pp. 813-820, 1998.

Stefano et al., "Macrophage Behavior Associated with Acute and Chronic Exposure to HIV GP120, Morphine and Anandamide: Endothelial Implications," International Journal of Cardiology, vol. 64, Suppl. 1, pp. S3-S13, 1998.

Stefano et al., "The Presence of the μ3 Opiate Receptor in Invertebrate Neural Tissues," Comp. Biochem. Physiol., vol. 113C, No. 3, pp. 369-373, 1996.

Bilfinger et al., "Direct Assessment and Diminished Production of Morphine Stimulated NO by Diabetic Endothelium from Saphenous Vein," Acta Pharmacologica Sinica, vol. 23, No. 2, pp. 97-102. Feb. 2002.

Stefano et al., "Cell-Surface Estrogen Receptors Mediate Calcium-Dependent Nitric Oxide Release in Human Endothelia," Circulation, vol. 101, pp. 1594-1597, 2000.

Chen, S. et al., "Molluscicidal Saponins from Allium Vineale," Tetrahedron Letters, vol. 28, No. 46 (1987), pp. 5603-5606.

Surh, Y.-J. et al., "Molecular mechanisms underlying chemopreventive activities of anti-inflammatory phytochemicals: down-regulation of COX-2 and iNOS through suppression of NF-kB activation," Mutation Research 480-481 (2001), pp. 243-268.

Murphy, L.L. et al., "Ginseng, Sex Behavior, and Nitric Oxide," Ann. N.Y. Acad. Sci. 962 (2002), pp. 372-377.

Wang, M. et al., "Immunomodulating activity of CVT-E002, a proprietary extract from North American ginseng (Panax quinquefolium)," Journal of Pharmacy and Pharmacology 53 (2001), pp. 1515-1523.

Kim, H.-M. et al., "Activation of inducible nitric oxide synthase by Taraxacum officinale in mouse peritoneal macrophages," General Pharmacology 32 (1999), pp. 683-688.

Yuan, C.-S. et al., "Panax Quinquefolium L. Inhibits Thrombin-Induced Endothelin Release In Vitro," American Journal of Chinese Medicine, vol. XXVII, Nos. 3-4 (1999), pp. 331-338.

Boveris, A. et al., "Effect of nitric oxide and plant antioxidants on microsomal content of lipid radicals," Biol. Res. 33 (2000), pp. 159-165.

Author Unknown, "Monograph: Taraxacum officinale," Alternative Medicine Review, vol. 4, No. 2 (1999), pp. 112-114.

The Patent Office of the People'S Republic of China, "Notification of the Second Office Action", Application No. 200610148573.4, Date of Notification Oct. 30, 2009.

Baba et al., "Antitumor Activity of Hot Water Extract of Dandelion", Pharmacy Magazine (Japan), vol. 101, No. 6, pp. 538-539, Dec. 31, 1981.

\* cited by examiner

NITRIC OXIDE AND ITS BIOMEDICAL SIGNIFICANCE

REFERENCE TO PRIOR APPLICATION

This application claims the benefit of co-pending P.C.T. Application No. PCT/US2003/25966, filed on Aug. 19, 2003, and U.S. Provisional Application Ser. No. 60/405,787, filed on Aug. 23, 2002, and hereby incorporated herein by reference.

INVENTION FIELD

This invention discloses materials and methods involved in the production of nitric oxide. Specifically, the invention relates to low molecular weight, water soluble, molecules isolated from plant tissue and materials and the use of these molecules to induce nitric oxide production in mammalian cells and tissues.

INVENTION BACKGROUND

Nitric oxide (NO) is a major signaling molecule in the mammalian immune, cardiovascular and nervous systems.[18,26,37,56,57,109] NO produced at one site can have an effect on tissues at a distance.[24,70] NO is produced from L-arginine by the enzyme, nitric oxide synthase (NOS).[55,57] NOS occurs in three forms: endothelial (e), neuronal (n), and inducible (i) NOS. The first two forms are constitutively expressed and $Ca^{2+}$ dependent. Inducible (i) NOS is $Ca^{2+}$ independent. The three forms of NOS are encoded for on three distinct genes on chromosomes, 7, 12, and 17, respectively.[18,26,37,54] In general, n- and e-NOS depend on intracellular calcium transients and release NO in the nM range, whereas iNOS, following an induction/latency period, can release NO in the µM range for extended periods of time.[18,26,28,37,56,57,70,105,109] The presence of constitutive and inducible forms of NOS suggest that they may have distinct functions.

c- and i- NOS can be distinguished on the basis of the length of time necessary to see an increase in levels of NO and the length of time these elevated levels can be maintained. NO derived from cNOS may occur in two functional forms: the first is always present at low "tonal" or "basal" levels; this basal level can be slightly increased for a short time in response to certain signals, e.g., acetylcholine (ACH).[56] This brief enhanced release of cNOS derived NO can have profound physiological actions, which are evident long after NO has returned to its basal level, for a longer period of time.[50] For example, endothelial cells briefly exposed to morphine and eNOS change their shape from elongated to round, a process that takes several hours.[50]

iNOS is induced by various signal molecules, e.g., proinflammatory cytokines.[57,73,105] The induction of i-NOS is usually seen after a 3-4 hour delay; iNOS is capable of producing NO for 24-48 hours.[73,105] These data suggest that NO is always present and that the levels of NO can be regulated either rapidly or slowly depending on the organism's needs. The presence of different regulatory processes implies that NO has different functions, and/or that the levels of NO must be progressively increased in order for it to exert its function.

NO functions as a vascular, immune and neural signal molecule and also has general antibacterial, antiviral actions and the ability to down-regulated proinflammatory events.[38-39,41-42,60,90,105-106] In the vascular and immune system, one of the key stages in the immune response is the recruitment and activation of leukocytes by the endothelium. Leukocyte activation by the endothelium occurs in stages. The initial step is the attraction of the leukocytes to the endothelium. This is followed by increased leukocyte adhesion and change in shape and finally migration across the endothelium.[90] These cellular changes are accompanied by scheduled changes in synthesis of molecules that regulate cell-matrix interactions.[3,46,52,87]

Normally, non-activated leukocytes roll along the endothelium. The interaction between the two cell types is loose and reversible and mediated by a family of adhesion molecules known as selectins. Activation of leukocytes occurs in response to the release of several chemoattractants including leukotriene $B_4$ and interleukin 8 (IL-8). In the presence of these agents, immunocytes cease to roll, becoming "activated": they start to flatten and adhere with greater strength to the endothelial lining. Activation is mediated by a family of adhesion molecules call the integrins, such as ICAM-1 and VCAM-1. Adherent immunocytes are able to undergo transendothelial migration in the presence of PECAM-1.[3,46,52,87] This immunocyte-endothelial interaction is down-regulated by NO. NO inhibits platelet and neutrophil aggregation and can diminish the adherence and level of activation of leukocytes and endothelial cells.[41,1,50,109] NOS inhibitors increase platelet adhesion and enhance leukocyte adhesion.[72,82] NO plays a similar role involving the microglia cells of the nervous system's immune response.[83,84]

The central nervous system (CNS) is unique in that it uses all three isoforms of NOS to produce NO. The constitutive isoforms e- and n- NOS are found in the normal CNS; however, iNOS is not expressed in the healthy CNS.[20] Pathological states, e.g., trama, cerebral ischemia and neuronal diseases, increase the levels of e- and nNOS and induce iNOS activity.[21] cNOS derived NO has the ability to down-regulate proinflammatory events via inhibition of NF-κB activation of proinflammatory cytokines.

NO upregulates several enzymes involved in immunoregulation, including neutral endopeptidese 24.11 (CALLA, acute lymphoblastic leukemic antigen, enkephalinase) or CD10.[76] Thus, cNOS derived No stimulates enzymes that process protein gene products, implying a link between signaling processes involving NO and naturally occurring antibacterial peptides. No controls and regulates enzymes that are responsible for liberating these crucial molecules that have a proactive protective function.[101]

Evidence has also been provided that NO plays a role in neurotransmitter release.[102] Morphine and cNOS derived NO release growth hormone and ACTH from rat brain fragments; these neuropeptides are involved in the stress response. Thus, NO is involved in vasodilation, antibacterial and antiviral responses, signal molecule release and inhibition of immunocyte adherence to the endothelium.

There appears to be a tonal or basal level of NO that is physiologically significant. Endothelia from non-insulin dependent diabetics do not exhibit a tonal level of NO[117] and in these individuals vascular disease causes disability and eventual death.[14] A number of researchers have attributed vascular disease in part to alterations associated with eNOS-derived NO and some have speculated this may be due to enhanced free radical generation.[59] Decreases in basal NO levels may also contribute to enhanced platelet function and various neuropathies.[32,68]

Thus, it appears that tonal or basal NO levels are important in limiting the degree of excitation of nervous, immune and vascular tissues. This tonal NO may manifest itself via effects on adhesion-mediated processes via NF-κB. Estrogen may exert it beneficial vascular protective actions via these processes as well, since it also releases cNOS derived NO.[70,99] Strengthening this hypothesis in the finding of the cannabinoid CB1 receptor type on mammalian endothelial cells[118, 119] and the finding of a mu opiate receptor on human vascular endothelial cells. (Three general classes of cell surface opioid receptors (kappa, delta and mu) have been described. Receptors exhibiting high binding specificity for morphine have been designated mu opioid receptors.) Detailed analysis has revealed the existence of multiple mu opioid receptor subtypes. Isolated nucleic acid sequences encoding various mu receptors and polypeptides comprising mu receptors (and referred to here as "mu3 opioid receptor(s)") are disclosed in detail in PCT Patent Publication WO 99/24471, published 20 May 1999. See also, Molecular Identification and Functional Expression of $\mu_3$, a Novel Alternatively Spliced Variant of the Human $\mu$ Opiate Receptor Gene.

Consequently, promoting NO generation at normal or slightly enhanced levels may have significant health value. While the health promoting effects of many plants are well known, how and why this occurs at a molecular level is less understood. See Stefano and Miller, Communication between animal cells and the plant foods they ingest: Phytozooidal dependencies and signalling (Review), *Intl J Mol Medicine* 10: 413-21 (2002) incorporated by reference herein.

INVENTION SUMMARY

The invention relates to nitric oxide (NO) stimulating extracts from various plants. Such extracts contain compounds known as healthin I and healthin II. Specifically, the invention provides partially purified plant extracts that have NO stimulating activity, methods of isolating and partially purifying such extracts from plant materials. In addition, the invention provides methods and materials for treating diseases and conditions that require modification of cellular levels of NO, for example, diseases and conditions involving inflammation.

The invention is based on the discovery of a class of agents identified by extraction and chemical analysis of certain plant species that are capable of stimulating NO production in mammalian cells and tissues. These NO stimulating agents stimulate the production of constitutive nitric oxide synthase in mammalian vascular endothelial cells and/or neuronal cells in culture.

Accordingly, the invention provides active, chemical agents isolated from plant tissue and materials that stimulate the production of nitric oxide in pedal ganglia and human endothelial cells. Partially purified extracts from any of the plants listed below contain various amounts of the active agents.

In addition, the invention provides methods and materials for identifying additional NO stimulating botanical agents from other plants having such activity and methods and materials useful in the treatment of diseases and conditions requiring modification of cellular levels of NO.

These botanical agents of the invention are additionally characterized as having:
  (i) the ability to stimulate nitric oxide release in the range of 15 nM to 100 nM in pedal ganglia cells;
  (ii) the ability to stimulate nitric oxide release in the range of 50 nM to 100 nM in endothelial cells;
  (iii) a single major peak on high performance liquid chromatographic analysis in 10 nM sodium chloride, 0,5 mM EDTA, 100 mM sodium acetate and 50% acetonitrile, pH 5.0.

The NO stimulating botanical agents of the invention may be further characterized by being water soluble and having a molecular mass of between about 50 and about 5000 Daltons, or between about 50 and about 2500 Daltons, or between about 50 and about 1000 Daltons, or between about 50 and about 500 Daltons.

The botanical agents of the invention can be extracted from plants selected from the group consisting of *Agropyrum* spp., *Salix alba*, *Allium vineale*, *Petroselinium crispum*, *Taraxacum officinale*, *Sesamum indicum*, *Medicago* spp., *Piper methysticum*, *Anthemis* spp., *Turnera diffusa*, *Verbascum densiflorum*, *Ocimum* spp., *Maranta arundinaceae*, *Coriandrum Sativum*, *Artemesia dracunculus*, *Lavendula augustifolia*, *Mentha pulegium*, *Centella asiatica*, *Ginko biloba*, and *Vitus vinifera*.

Accordingly, one aspect of the invention is a pharmaceutical composition consisting of low molecular weight, water soluble, extract of at least one of the following plants: *Allium vineale*, *salix alba*, *Agropyrum* spp., *Petroselinium crispum*, *Taraxacum officinale*, *Sesamum indicum*, *Medicago* spp., *Piper methysticum*, *Anthemis* spp., *Turnera diffusa*, *Verbascum densiflorum*, *Ocimum* spp., *Maranta arundinaceae*, *Coriandrum sativum*, *Artemesia dracunculus*, *Lavendula augustifolia*, *Mentha pulegium*, *Centella asiatica*, *Ginko biloba* and *Vitis vinifera*, which extracts have nitric oxide stimulating ability in mammalian cells. These extracts are additionally characterized as having the ability to stimulate nitric oxide release in the range of 15 nM to 100 nM in pedal ganglia cells and/or the ability to stimulate nitric oxide release in the range of 50 nM to 100 nM in endothelial cells. These extracts are also characterized by having components greater than 5000 Daltons removed, i.e., by comprising low molecular weight water soluble components in the range of about 50 to 5000 Daltons. More preferably, components greater than 2500 Daltons are removed and water soluble components in the range of about 50 to about 2500 Daltons are included. Most preferably, components greater than 1000 Daltons are removed and water soluble components in the range of about 50 to about 1000 Daltons are included. Especially preferred are extracts having water soluble components in the range of about 50 to about 500 Daltons. These extracts are additionally characterized as exhibiting a single major peak on high performance liquid chromatographic analysis in 10 nM sodium chloride, 0,5 mM EDTA, 100 mM sodium acetate and 50% acetonitrile, pH 5.0.

These extracts may be dried and formed into pharmaceutical compositions comprising powders, tablets, poltices, pastes, creams, plasters, capsules and the like, with or without pharmceutically acceptable excipients and/or adjuvants, in accordance with known methods and techniques, for example, as detailed in Remington's Pharmaceutical Sciences, A. R. Gennaro, ed., Mack Publ. Co. Easton, Pa., 1985.

Another aspect of the invention is to provide a method for identifying and isolating low molecular weight extracts of at least one of the plants set forth above, which extracts exhibit NO stimulating activity in mammalian cells.

A further aspect of the invention is to provide a method of using low molecular weight extracts of at least one of the plants set forth above, which extracts exhibit NO stimulating activity in mammalian cells.

An additional aspect of the invention is a method for preparing an NO stimulating extract of at least one of the plants set forth above by preparing an aqueous extract having components being water soluble and having a molecular mass of between about 50 and about 5000 Daltons, or between about 50 and about 2500 Daltons, or between about 50 and about 1000 Daltons, or between about 50 and about 500 Daltons.

Other features and advantages will be apparent from the following detailed description, drawings and claims.

DRAWING DESCRIPTIONS

FIG. 7 and FIG. 8 illustrate the results of the pedal ganglia and endothelial cell stimulation by *Salix alba* extracts as detailed in Example 6.

DETAILED DESCRIPTION

The invention provides active, chemical agents isolated from plant tissue and materials that stimulate the production of nitric oxide in pedal ganglia and human endothelial cells. Low molecular weight, water soluble, extracts from any of the plants listed below contain various amounts of the active chemical agents that stimulate production of NO. In addition, the invention provides methods and materials for identifying and isolating additional NO stimulating botanical agents from other plants having such activity and methods and materials useful in the treatment of diseases and conditions requiring modification of cellular levels of NO.

These botanical extracts of the invention are additionally characterized as having:
(iv) the ability to stimulate nitric oxide release in the range of 15 nM to 100 nM in pedal ganglia cells;
(v) the ability to stimulate nitric oxide release in the range of 50 nM to 100 nM in endothelial cells; and/or
(vi) a single major peak on high performance liquid chromatographic analysis in 10 nM sodium chloride, 0.5 mM EDTA, 100 mM sodium acetate and 50% acetonitrile, pH 5.0.

The NO stimulating botanical agents of the invention may be further characterized by being water soluble and having a molecular mass of between about 50 and about 5000 Daltons, or between about 50 and about 2500 Daltons, or between about 50 and about 1000 Daltons, or between about 50 and about 500 Daltons.

The extracts of the invention can be isolated from plants selected from the group consisting of *Allium vineale, salix alba, Agropyrum* spp., *Petroselinium crispum, Taraxacum officinale, Sesamum indicum, Medicago* spp., *Piper methysticum, Anthemis* spp., *Tumera diffusa, Verbascum densiflorum, Ocimum* spp., *Maranta arundinaceae, Coriandrum sativum, Artemesia dracunculus, Lavendula augustifolia, Mentha pulegium, Centella asiatica, Ginko biloba* and *Vitis vinifera*.

The method of isolating and extracting to obtain the active component comprises homogenizing dried plant material in an acidic solution followed by alcohol extraction and centrifugation for filtration to separate the solid material. The supernatant is dried and then dissolved in an aqueous solution containing trifluroacetic acid and subjected to solid phase extraction. The elute is collected and further purified using high performance liquid chromatography. The extracted active component can be further identified and characterized by mass spectrometric analysis.

The method of identifying NO stimulating botanical agents of the invention comprises homogenizing dried plant material in an acidic solution followed by alcohol extraction and centrifugation, again for filtration to separate the solid material. The supernatant is dried and then dissolved in an aqueous solution containing trifluroacetic acid and subjected to solid phase extraction. The elute is collected and further purified using high performance liquid chromatography and the extracted, low molecular weight, NO stimulating agents are identified by mass spectrometric analysis.

These extract are useful in the preparation of pharmaceutical compositions for treating antimicrobial infections such as bacterial infections and viral infections, and asthma, and/or other inflammatory conditions in mammals, especially in humans. The extracts, as detailed below, exhibit antibacterial, antiinflammatory and anticancer effects. Consequently, pharmaceutical compositions comprising such extracts can be administered in the treatment various diseases and conditions in which antibacterial, antiinflammatory or anticancer effects are desired, such as for example, in microbial infections. Alternatively, the pharmaceutical compositions of the invention may be employed as prophylactics. To form the extracts into pharmaceutical compositions, they may be dried, alone or in various combinations, and formed into pharmaceutical compositions comprising powders, tablets, poltices, pastes, creams, plasters, capsules and the like, with or without pharmnceutically acceptable excipients and/or adjuvants, in accordance with well known methods and techniques, for example, as detailed in Remington's Pharmaceutical Sciences, A. R. Gennaro, ed., Mack Publ. Co. Easton, Pa., 1985.

The invention will be further described in the following examples, without limiting the scope of the invention as described in the claims. In the examples, the plant extracts were made from the leaves of the plant, unless otherwise specified.

EXAMPLES

Example 1

Extraction of Healthin I from Wheat Grass

One grams of dried wheat grass plants, Agropyron spp. were homogenized in 1N HCl (0.5 g/ml). The resulting homogenates were extracted with 5 ml chloroform/isopropanol 9:1. After 5 min at room temperature, homogenates were centrifuged at 3000 rpm for 15 min. The supernatant was collected and dried with a Centrivap Console (Labconco, Kansas City, Mo.). The dried extract was then dissolved in 0.05% trifluoroacetic acid (TFA) water before solid phase extraction. Samples were loaded on a Sep-pak Plus C-18 cartridge (Waters, Milford, Mass.) previously activated with 100% acetonitrile and washed with 0.05% TFA-water. Morphine elution was performed with a 10% acetonitrile solution (water/acetonitrile/TFA, 89.5%: 10%: 0.05%, v/v/v). The eluted sample was dried with a Centrivap Console and dissolved in water prior to high performance liquid chromatography analysis (HPLC).

Reverse phase HPLC analysis using a gradient of acetonitrile was performed on a C-18 Unijet microbore column (BAS, West Lafayette, Ind.) using a Waters 626 pump (Waters, Milford, Mass.). 0.025 g dry weight of the wheat grass from the above-described extraction was used. The mobile phases were: Buffer A: 10 mM sodium chloride, 0.5 mM EDTA, 100 mM sodium acetate, pH 5.0; Buffer B: 10 mM sodium chloride, 0.5 mM EDTA, 100 mM sodium acetate, 50% acetonitrile, pH 5.0. A flow splitter (BAS), with split ratio 1/9 was used to provide the low volumetric flow rates required for the microbore column. Operating the pump at 0.5 ml/min yielded a microbore column flow rate of approximately 50 µl/min. The injection volume was 5 µl. The running conditions were: 0 min, 0% Buffer B; 10 min, 5% Buffer B; 25 min, 50% Buffer B; 30 min, 100% Buffer B. Both buffers were filtered through a Waters 0.22 µm filter and the temperature of the system was maintained at 25° C. The active agent (Healthin 1) extracted from the wheat grass had a retention time of 15.8 min (see arrow on FIG. 1). This result was repeated in 5 extractions. Several blank runs were performed between each of the 5 sample runs to prevent residual chromatography corresponding to the elution of the active component.

Figure 1:
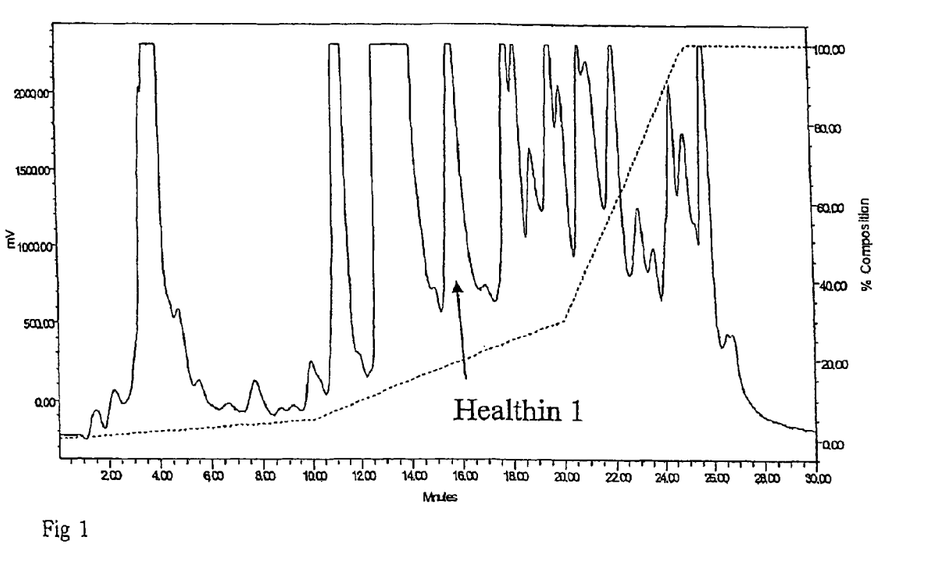
FIG. 1 is a reproduction of the HPLC chromatogram of the wheat grass extraction detailed in Example 1.

Active component detection was performed with an amperometric detector LC-4C (BAS). The microbore column was coupled directly to the detector cell to minimize the dead volume. The electrochemical detection system used a glassy carbon-working electrode (3 mm) and a 0.02 Hz filter (500 mV; range 10 nA). The cell volume was reduced by a 16 µm gasket. The chromatographic system was controlled by the Waters Millennium chromatography Manager V3.2 software and the chromatograms were integrated with Chromatograph software (Waters). The concentration was extrapolated from the peak area. The average concentration in the 5 samples was 1 µg/gm dry weight. Blank runs between determinations failed to elicit carry over residue. The fractions from each of the 5 runs were collected, dried and applied in the NO tissue assays described below. Results are illustrated in FIG. 1.

An alternative method of purification was performed by methanol extraction followed by HPLC purification on a Spherisorb column as follows. One gram of wheat grass, *Agropyron* spp, was homogenized in 50% methanol, 50% purified water, extracted with 50% methanol, and dried by speed vacuum. The sample was stored at −20° C. HPLC purification was carried out with a two solvent system: Buffer A was composed of 10 mM 1-heptane sulfonic acid, sodium salt and 10 mM sodium phosphate monobasic water, pH 3; Buffer B was composed of 10 mM 1-heptane sulfonic acid, sodium salt and 10 mM sodium phosphate monobasic, 50% methanol. The injection volume was 10 microliters. The running conditions were: 0-10 min, 50% Buffer B; 10-20 min, Buffer B increased from 50 to 100%; 25 min, 100% Buffer B; 35 min, 50% Buffer B. Fractions were collected from 0 to 30 minutes after sample injection. The collected fractions were dried by speed vacuum and maintained at −20° C. The active agent extracted from the wheat grass had a retention time of 16 min (see arrow on FIG. 1*a*).

Example 2

Extraction of Healthin II from White Willow Bark

Figure 2:
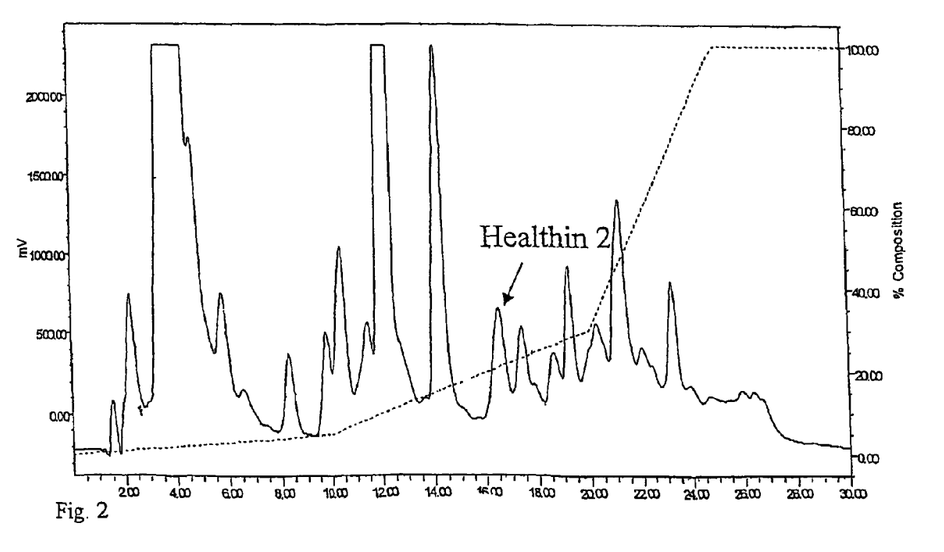
FIG. 2 is a reproduction of the HPLC chromatogram of the white willow bark extraction detailed in Example 2.

The identical procedure was performed with 0.02 grams (dry weight) of white willow bark, *Salix alba*, The active agent (Healthin 2) extracted from the white willow bark had a retention time of 16.50 min. The average concentration in the 5 samples sun was 0.3 µg/gm dry weight. See FIG. 2.

Example 3

Mass Spectrometric Identification of Active Agents from Agropyron

Figure 3:
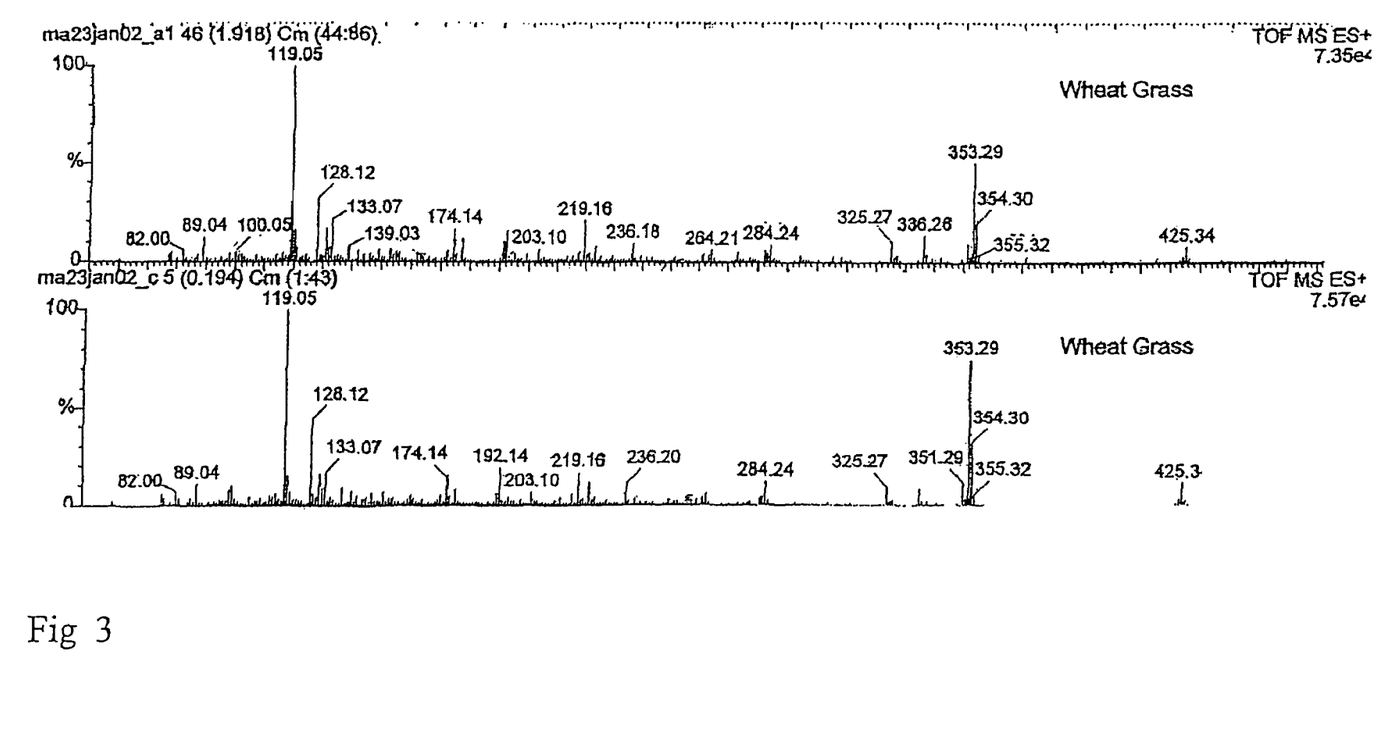
FIG. 3 is a reproduction of the data print out from the mass spectrometric analysis detailed in Example 3.

The HPLC fraction, 1/100 microliters, containing the NO releasing activity from the first purification detailed in Example 1 above was subjected to nano electrospray ionization double quadrupole orthogonal acceleration Time of Flight mass spectrometry (Q-TOF-MS) on a Micromass Q-TOF system (Micromass, UK) as follows. One µl of acetonitril/water/formic acid (50:49:1, v/v/v) containing the sample was loaded in a gold-coated capillary Micromass F-type needle. The sample was sprayed at a flow rate of 30 nl/min, giving an extended analysis time during which MS spectrum and several MS/MS spectra were acquired. During MS/MS, or tandem mass spectrometry, fragmentations are generated from a selected precursor ion by collision-induced dissociation (CID). Since not all ions fragment with the same efficiency, the collision energy is typically varied between 20 and 35 V, so that the parent ion is fragmented into a satisfying number of different daughter ions. Needle voltage was set at 950 and cone voltage was set at 25. The instrument was operated in the positive mode. The results are illustrated in FIG. 3. Healthin I, the active agent isolated and purified from the wheat grass sample, yielded major signals at 353.28 and 119.05 daltons.

Example 4

Mass Spectrometric Identification of Active Agents from *Salix alba*

Figure 4:
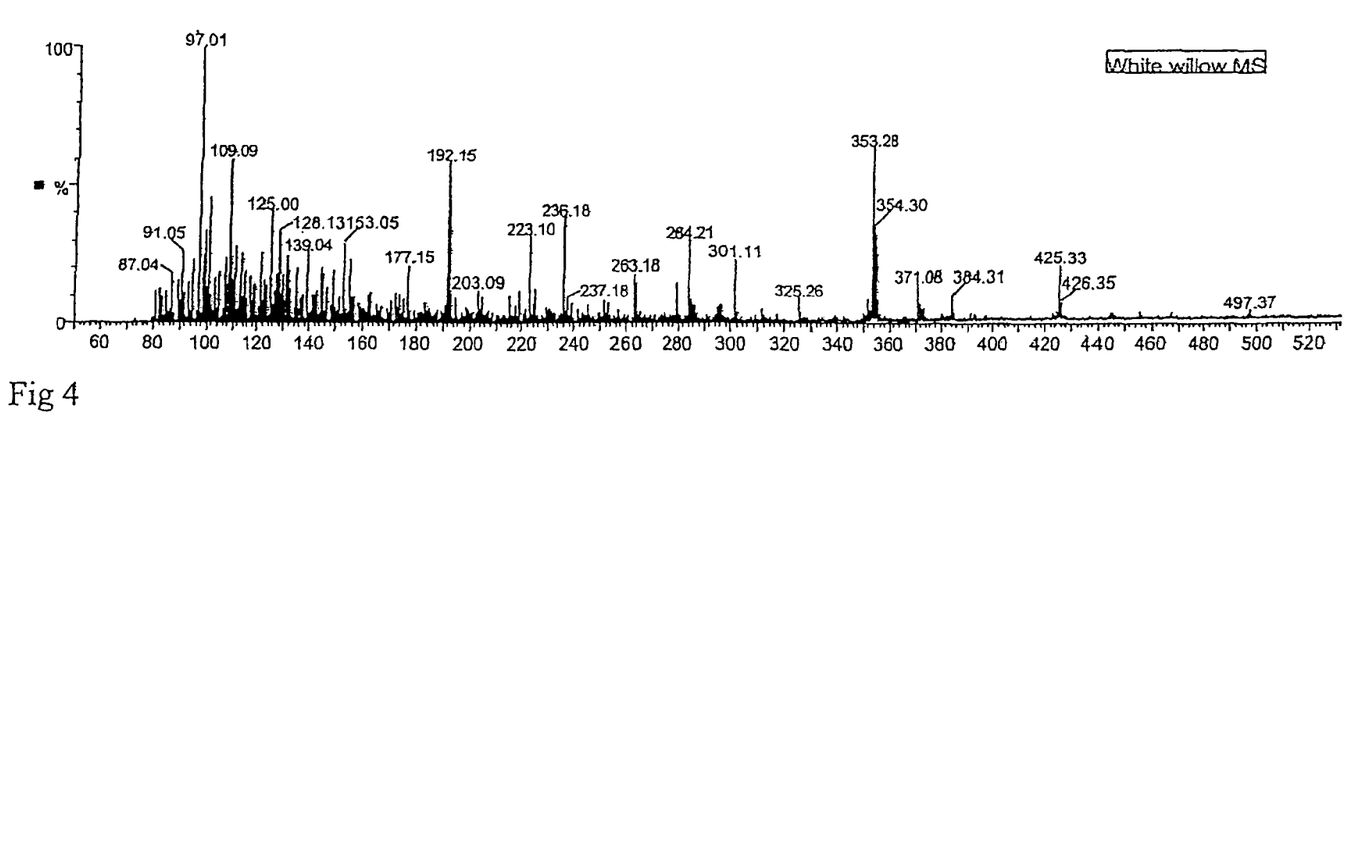
FIG. 4 is a reproduction of the data print out from the mass spectrometric analysis detailed in Example 4.

The identical procedure from Example 3 was performed with one gram of white willow bark, *Salix alba*. The results are shown in FIG. 4. Healthin II, the active agent isolated and purified from white willow bark sample, yielded major signals at 353.28, 192.15, 109.09 and 97.1 daltons.

Example 5

Agropyron Extract Stimulation of NO in Pedal Ganglia and Endothelial Cells

Ten *Mytilus edulis* pedal ganglia, dissected from live animals, were placed in 1.5 ml Eppendorf tubes with 990 µl of phosphate buffer saline (PBS). Cultured human vein endothelial cells (ATCC # CRL 1730) were washed in PBS at 4° C. The vein endothelial cells were grouped into patches of approximately $10^6$ cells each and placed in 990 µl of PBS at 4° C. One gram of dried wheat grass, *Agropyron* spp, was purified by HPLC as detailed above and the fraction corresponding to the retention time of the Healthin 1 was collected and dried. The fraction was then reconstituted in 20 µl PBS. 10 µl were added to the tubes containing the ganglia or the endothelial cells or PBS alone (control). NO production was determined using a Mark II isolated nitric oxide meter (World Precision Instruments, Sarasota, Fla.) fitted with a 200 µM sensor. If a response was detected in the tube containing PBS alone, the amount was subtracted from the amounts detected in the tubes containing the tissue samples.

Figure 5:
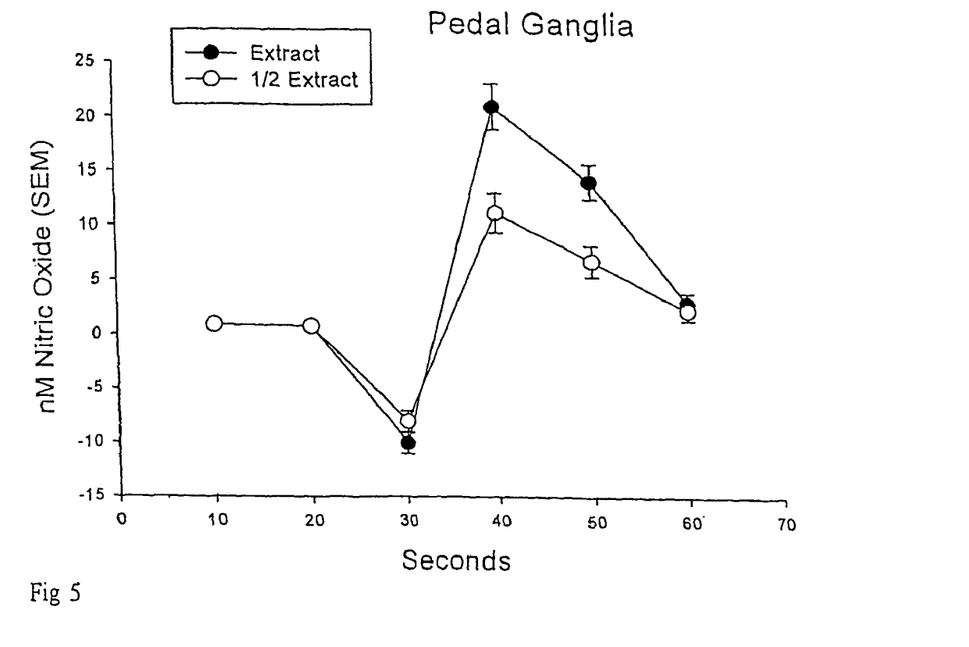
FIG. 5 and FIG. 6 illustrate the results of the pedal ganglia and endothelial cell stimulation by *Agropyrum* spp. plant extracts as detailed in Example 5.
Figure 6:
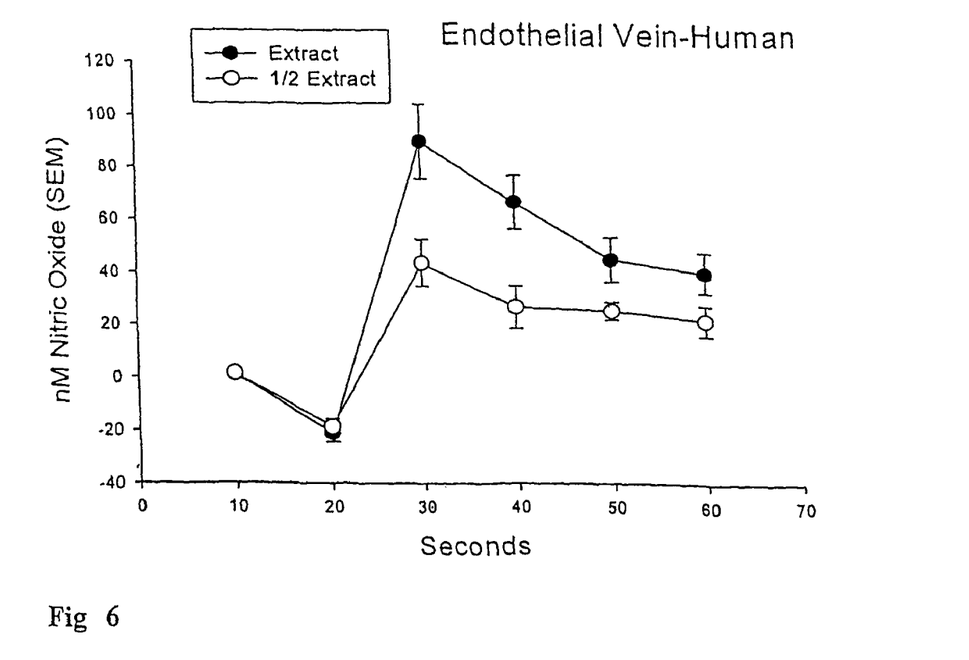

The results are shown in FIGS. 5 and 6. The pedal ganglia tube cells released 17 nM NO (FIG. 5), the human endothelial cells released 91 nM NO (FIG. 6). The identical volume added to the control tube resulted in the production of <3 nM NO.

Example 6

*Salix alba* Extract Stimulation of NO in Pedal Ganglia and Endothelial Cells

Figure 7:
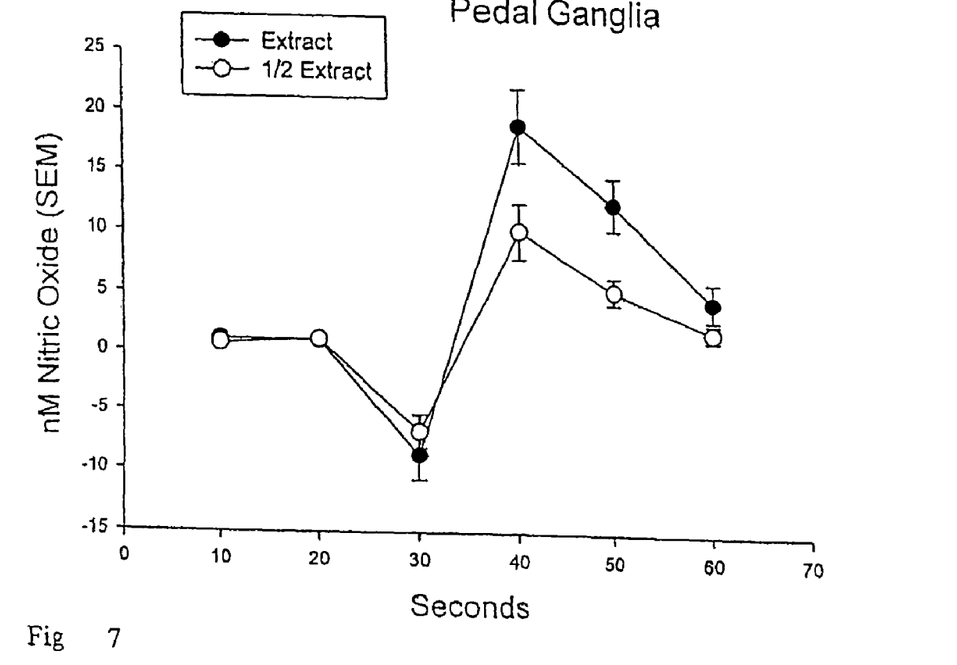

The procedure detailed in Example 5 above was performed with one milligram of the agent purified from the white willow bark, *Salix alba*, from Example 2. The results are shown in FIGS. 7 and 8. The pedal ganglia tube cells released 19 nM NO (FIG. 7), the human endothelial cells released 87 nM NO (FIG. 8). The identical volume added to the control tube resulted in the production of <3 nM NO.

Example 7

Analysis of Plants of Various Species for NO Release

Figure 9:
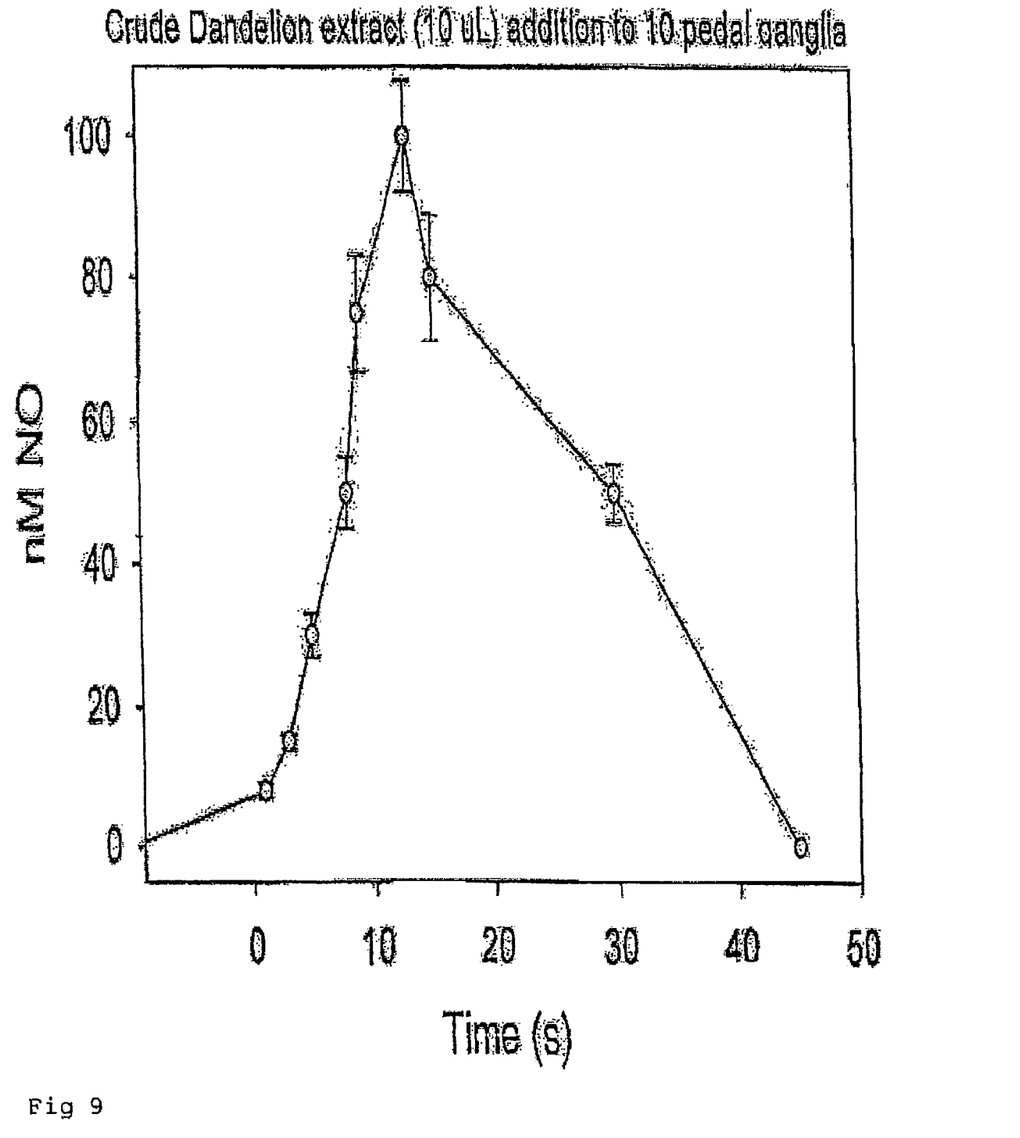
FIG. 9 illustrates the results of the pedal ganglia cell stimulation by *Taracum officinale* extracts as detailed in Example 7.

Employing the isolation and purification techniques described above, a variety of herbaceous plants were analyzed for their ability to release cNOS- derived nitric oxide in the pedal ganglia and in publicly available SK-N-MC (ATCC # HBT-10) and PC-12 (ATCC # CRL 1721) cells. These results are set forth in Tables I, II, and III below. In Table I, a plus sign indicates detection of at least 1 nM nitric oxide. A minus sign indicates no detection or detection of less than 1 nM nitric oxide. In Table II, results in the SK-N-MC cell line are set forth; the concentration of plant material used and the quantity of NO detected is indicated. In Table III, results are set forth for the identical procedures performed using the ganglia cell line. The types of plant materials employed are indicated, for example flowers, leaves, roots, rhizomes, stems, bark. Where not specified, leaves were employed. FIG. 9 shows an exemplary result.

TABLE I

NO determination of ganglia, SK-N-MC and PC-12 cells treated with various plant extractions. Blank indicates plant not tested in that cell line.

| | Ganglia | SK-N-MC | PC-12 |
|---|---|---|---|
| *Allium vineale* (Garlic) | — | + | |
| *Salix alba* (White willow) bark | + | + | |
| *Agropyron* (Wheat grass) | + | + | |
| *Petroselinium crispum* or *Carum petroselinum* (Parsley) | — | + | |
| *Taraxacum officinale* (Dandelion) | + | — | |
| *Sesamum indicum* (Sesame, Gin sum) leaves | | + | |
| *Medicago* spp. (Alfalfa) | | + | |
| *Piper methysticum* (Kava) | | + | |
| *Anthemis* spp. (Chamomile) | +++ | + | |
| *Turnera diffusa* (Damian) | | + | |
| *Verbascum densiflorum* (Mullein) | | + | |
| *Maranta arundinaceae* (Arrowroot) roots | | — | |
| *Lavandula angustifolia* (Lavender) flower | | — | |
| *Ocimum* spp. (Sweet basil) | | — | |
| *Artemesia dracunculus* (Tarragon) leaves | | — | |
| *Aloe vulgaris* or *A. barbadensis* (Aloe) leaves | — | — | |
| *Vacciuium membranaceum* (Bilberry) | — | — | |
| *Brassica* spp. (Cabbage) | — | — | |
| *Daucus carota* (Carrot) | — | — | |
| *Zea mays* flowers (corn silk) | — | — | |
| *Echinacea* (Coneflower) | — | — | |
| *Lactuca* spp. (Lettuce) | — | — | |
| *Tabebuia impetiginosa*, *T. avellanedai*, *Tecoma curialis* (Pau d'arco) | — | — | |
| *Mentha piperita* (Peppermint) | — | — | |
| *Rubus* spp. (Raspberry) | — | — | |
| *Rosmarinus officinalis* (Rosemary) | — | — | |
| *Salvia* spp. (Sage) | — | — | |
| *Equisetum hyemale* (Shave grass) | — | — | |
| *Ulmus rubra*, *Fremontodendron californicum* (Slippery elm) bark | — | — | |
| *Phaseolus* spp. (String bean) | — | — | |
| *Thymus* spp. (Thyme) | — | — | |

TABLE II

NO determination of SK-N-MC cells treated with various plant extractions

| | Concentration | Results (nM) |
|---|---|---|
| *Ocimum* spp. (Basil) | 6 mg of crude extraction | 31 |
| *Verbascum densiflorum* (Mullein) | 6 mg of crude extraction | No effect |
| *Tumera diffusa* (Damian) | 6 mg of crude extraction | No effect |
| *Maranta arundinaceae* (Arrowroot) root | 6 mg of crude extraction | 31 |
| *Coriandrum sativum* (Cilantro) | 6 mg of crude extraction | 172 |
| *Artemesia dracunculus* (Tarragon) | 6 mg of crude extraction | 135 |
| *Lavendula augustifolia* (Lavender) flower | 6 mg of crude extraction | 48 |
| *Mentha pulegium* (Pennyroyal) | 6 mg of crude extraction | 66 |
| Quercetine* | 6 mg of crude extraction | 14 |
| *Piper methysticum* (Kava) | 1.5 mg | 108 |
| *Anthemis* spp. (Chamomile) | 1.5 mg | 31 |
| *Centella asiatica* (Gotu kola) | 1.5 mg | Reactive in PBS |
| *Scutellaria lateriflora* (Skullcap) | 1.5 mg | Negative |
| *Ginko biloba* (Ginko) | 1.5 mg | Reactive in PBS |
| *Hypericum perforatum* (St John's Wort) | 1.5 mg | Negative |
| *Urtica dioeca* (Common nettle) | 1.5 mg | Negative |

*Quercetine (from Sigma Chemicals) is a plant flavanoid found in many plants, and especially in fruits.

TABLE III

NO determination of ganglia cells treated with various plant extractions

| *Anthemis* spp. (Chamomile) | 6 mg of crude extraction | 67 nM |
|---|---|---|
| *Piper methysticum* (Kava) root | 6 mg of crude extraction | 13 nM |
| *Turnera diffusa* (Damian) | 6 mg of crude extraction | 22 nM |
| *Verbascum densiflorum* (Mullein) | 6 mg of crude extraction | 15 nM |
| *Ocimum* spp. (Basil) | 6 mg of crude extraction | 19 nM |

Example 8

Grape Skin Extraction and NO Release

Figure 10:
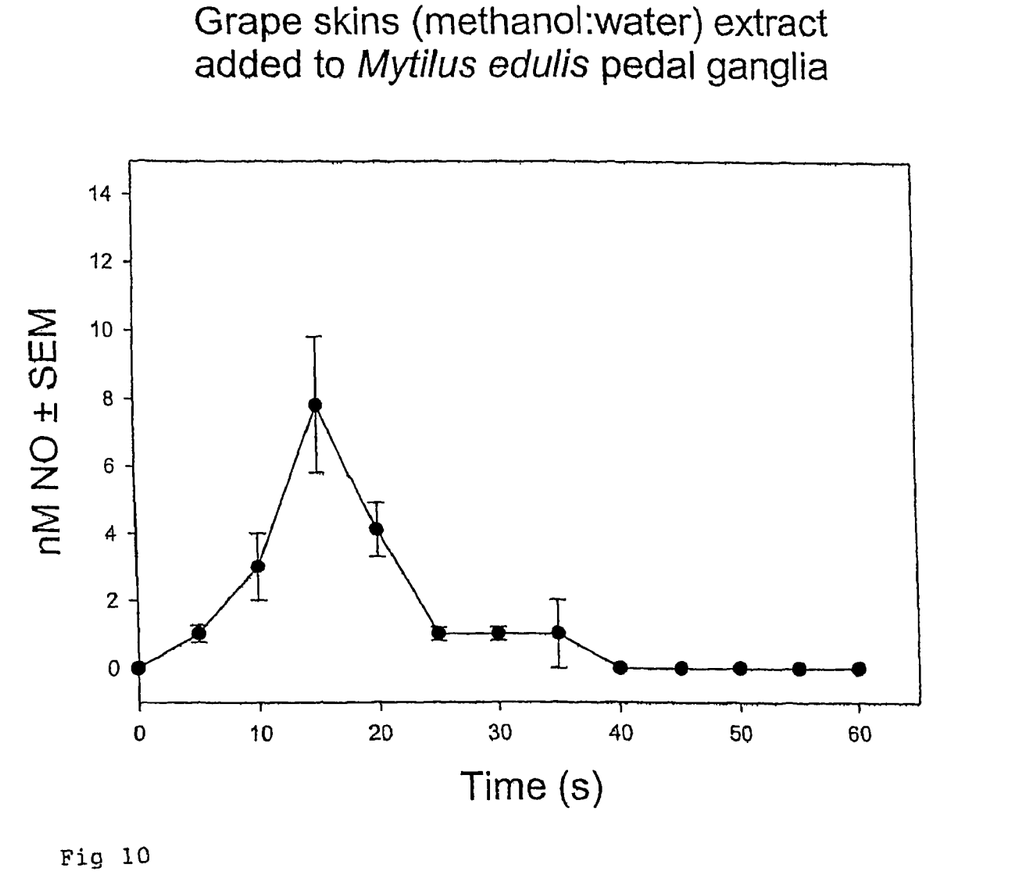
FIG. 10 illustrates the results of the pedal ganglia cell stimulation by *Vitus* extracts as detailed in Example 8.

Ten grams (wet weight) of black grape skins, *Vitis vinifera*, were placed in a 50 ml Falcon tube with 15 ml of a 1:1 mixture of methanol or ethanol and water. The tubes were shaken overnight at room temperature and the resulting extracts were aliquoted, 1 ml per tube, into twelve 1.5 ml Eppendorf tubes. The tubes were evaporated to dryness in a speedvac and then reconstituted in 1 ml phosphate buffered saline (PBS) solution. 10 µg o this solution was used to treat the invertebrate nervous tissue pedal ganglia (see Example 5, above) and NO release was measured in real time by an amperometric probe specific for the measurement of NO. Grape skin extracted in methanol caused a release of NO within 15 seconds of treatment (see FIG. 10) whereas grape skin extracted in ethanol did not (within the same time period). NO release was not observed when the extract (either methanol or ethanol extracted) was added to PBS alone.

Example 9

Anti-Microbial Effects of Extracts on Cells

A dried, powdered, formulation of a 1:1 mixture of the wheat grass extract and white willow bark extract prepared in Example 1 above was tested for its ability to inhibit bacterial growth in culture. The formulation was reconstituted in 10 ml of LB broth (Amersham Biosciences, Inc.). The broth was then inoculated with *E. coli* bacteria and incubated for 5 and 24 hours at 37° C. 20 µl of the cultures were streaked on LB-agar plates and incubated overnight at 37° C. There was no growth observed in the 5 and 24 hours bacterial cultures as compared to the control (LB broth alone).

An additional control experiment was conducted with the known antibacterial agent, SNAP. One µg/ml SNAP was added to LB broth. The broth was then inoculated with *E. coli* bacteria and incubated for 5 and 24 hours at 37° C. 20 µl of the cultures were streaked on LB-agar plates and incubated overnight at 37° C. Bacterial growth was decreased in the SNAP culture at 5 and 24 hours, as compared to the control.

This experiment demonstrates that the wheat grass/white willow extract of the invention exhibits greater antibacterial activity than the known antibacterial agent SNAP.

Example 10

Anti-Cancer Effects of Extracts on SK-N-MC Cells

SK-N-MC cells were incubated with either garlic (*Allium vineale*) or parsley (*Petroselinium crispum*) extractions, 0.005 g/ml in RPMI media, for two days. The cells were then stained with Trypan Blue indicator (Invitrogen Corp.) and observed under a research microscope at 200×. Healthy cells do not allow this indicator to enter the cell wall whereas cells which turn blue are dead or dying because the reagent has entered the cytoplasm. Microscope observation of both garlic and parsley treated cells indicated almost 100% of the cells were dead. Similar results were observed with 1 N solutions of Mullein (*Verbascum densiflorum*), Kava (*Piper methysticum*), Chamomile (*Anthemis* spp.), and Damian (*Turnera diffusa*). Other plant extracts prepared and tested in a similar manner that induced cell death in SK-N-MC cells were Bilberry (*Vaccinium myrtillus*), Enchinaceae purpurae, Garlic (*Allium vineale*), Goldenseal (*Hydrastis candensis*), Parsley (*Petroselenium crispum* or *C. petroselenium*), Paul d'arco bark (*Tabebuia impetiginosa*), Rosemary (*Rosmarinus officinalis*), Slippery elm (*Ulmus rubra* or *Fremontodendron califomicum*), and White willow bark (*Salix alba*). The strongest anti-cancer effects were seen with garlic and parsley.

Plant extracts prepared and tested in the same manner that exhibited no anti-cancer effect on SK-N-MC cells included Raspberry (*Rubus* spp.), Peppermint (*Mentha piperita*), Shave grass (*Equisetum hyemale*), cornsilk (*Zea mays* flowers), Dandelion (*Taraxacum officinale*), Alfalfa (*Medicago* spp.), Thyme (*Thymus* spp.) and Slippery Elm (*Ulmus rubra* and *Fremontodendron califomicum*).

References
1. Bath, P. M. W., Hasall, D. G., Gladwin, A. M., Palmer, R. M., and Martin, J. F. (1991): Nitric oxide and prostacyclin. Divergence of inhibitory effects on monocyte chemotaxis and adhesion to endothelium in vitro. *Arterioscler. Thromb.*, 11:254-260.
2. Bayon, Y., Alonso, A., and Sanchez Crespo, M. (1998): Immunoglobulin-E/dinitrophenyl complexes induce nitric oxide synthesis is rat peritoneal macrophages by a mechanism involving CD23 and NF-kappa B activation. *Biochem. Biophys. Res. Commun.*, 242:570-574.
3. Bevilacqua, M. P. (1993): Endothelial-leukocyte adhesion molecules. *Ann. Rev. Immunol.*, 11:767-804.
4. Bilfinger, T. V., Fricchione, G. L., and Stefano, G. B. (1993): Neuroimmune implications of cardiopulmonary bypass. *Adv. Neuroimmunol.*, 3:277-288.
5. Bilfinger, T. V., Hartman, A., Liu, Y., Magazine, H. I., and Stefano, G. B. (1997): Cryopreserved veins used for myocardial revascularization: a 5 year experience and a possible mechanism for their increased failure. *Ann. Thorac. Surg.*, 63:1063-1069.
6. Bilfinger, T. V., Kushnerik, V., Bundz, S., Liu, Y., and Stefano, G. B. (1996): Evidence for morphine downregulating immunocytes during cardiopulmonary bypass in a porcine model. *Int. J Cardiol.*, 53:S39-S46
7. Bilfinger, T. V., Salzet, M., Fimiani, C., Deutsch, D. G., and Stefano, G. B. (1998): Pharmacological evidence for anandamide amidase in human cardiac and vascular tissues. *Int. J. Cardiol.*, 64:S15-S22
8. Bilfinger, T. V. and Stefano, G. B. (1996): Cellular aspects of cardiopulmonary bypass surgery. *Int. J. Cardiol.*, 53S:R7
9. Bilfinger, T. V. and Stefano, G. B. (2000): Human aortocoronary grafts and nitric oxide release: Relationship to pulsatile pressure. *Annals of Thoracic Surgery*, 69:480-485.
10. Blackwell, T. S., Blackwell, T. R., Holden, E. P., Christman, B. W., and Christman, J. W. (1996): In vivo antioxidant treatment suppresses nuclear factor-kappa B activation and neutrophilic lung inflammation. *J. Immunol.*, 157:1630-1637.
11. Bodnar, A. and Pastemak, G. W. (1993): Aging and analgesic mechanisms. In: *Neuroregulatory Mechanisms in Aging*, edited by M. H. Makman, et al, pp. 137-158. Pergamon Press, Oxford.
12. Bone, R. C. (1991): The pathogenesis of sepsis. *Ann. Int. Med.*, 115:457-469.
13. Bredt, D. S. and Snyder, S. H. (1990): Isolation of nitric oxide synthase, a calmodulin-requiring enzyme. *Proc. Natl. Acad. Sci., USA*, 87:682-685.
14. Catalano, M., Carzaniga, G., Perilli, E., Jun, T., Scandale, G., Andreoni, S., and Carotta, M. (1997): Basal nitric oxide production is not reduced in patients with noninsulin-dependent diabetes mellitus. *Vascular Medicine*, 2:302-305.
15. Chen, C. C., Rosenbloom, C. L., Anderson, D. C., and Manning, A. M. (1995): Selective inhibition of E-selectin, vascular cell adhesion molecule-1, and intercellular adhesion molecule-1 expression by inhibitors of I kappa B-alpha phosphorylation. *J. Immunol.*, 155:3538-3545.
16. Clancy, R. M., Leszczynska-Piziak, J., and Abramson, S. B. (1993): Nitric Oxide stimulates the ADP-ribosylation of actin in human neutrophils. *Biochem. Biophys. Res. Commun.*, 191:847-852.
17. Colasanti, M., Persichini, T., Menegazzi, M., Mariotto, S., Giordano, E., Caldarera, C. M., Sogos, V., Lauro, G. M., and Suzuki, H. (1995): Induction of nitric oxide synthase m-RNA expression. Suppression by exogenous nitric oxide. *J. Biol. Chem.*, 270:26731-26733.
18. Cooke, J. P. and Dzau, V. J. (1997): Nitric oxide synthase: role in the genesis of vascular disease. *Ann. Rev. Med.*, 48:489-509.
19. Dawson, T. M. and Dawson, V. L. (1996): Nitric oxide synthase: role as a transmitter/mediator in the brain and endocrine system. *Ann. Rev. of Med.*, 47:219-227.
20. Dawson, V. L. and Dawson, T. M. (1995): Physiological and toxicological actions of nitric oxide in the central nervous system. *Adv. Pharmacol.*, 34:323-342.
21. Dawson, V. L. and Dawson, T. M. (1996): Nitric oxide neurotoxicity. *J. Chem. Neuroanatomy*, 10:179-190.
22. DeCaterina, R., Libby, P., Peng, H. B., Thannickal, V. J., Rajavashisth, T. B., Gimbrone, M. A., Jr., Shin, W. S., and Liao, J. K. (1995): Nitric oxide decreases cytokine-induced endothelial activation. Nitric oxide selectively reduces endothelial expression of adhesion molecules and proinflammatory cytokines. *J. Clin. Invest.,* 96:60-81.

23. Dembinska-Kiec, A., Zmuda, A., Wenhrynowicz, O., Stachura, J., Peskar, B. A., and Gryglewski, R. J. (1993): Selectin-P-mediated adherence of platelets to neutrophils is regulated by prostanoids and nitric oxide. *Intl. J. Tiss. Reactions,* 15:55-64.

24. Deutsch, D. G., Goligorsky, M. S., Schmid, P. C., Krebsbach, R. J., Schmid, H. H. O., Das, S. K., Dey, S. K., Stefano, G. B., Arreaza, R., Thorup, C., and Moore, L. (1997): Production and physiological actions of anandamide in the vasculature of the rat kidney. *Journal of Clinical Investigation,* 100:1538-1546.

25. Dobrenis, K., Makman, M. H., and Stefano, G. B. (1995): Occurrence of the opiate alkaloid-selective 3 receptor in mammalian microglia, astrocytes and kupffer cells. *Brain Res.,* 686:239-248.

26. Faraci, F. M. and Heistad, D. D. (1998): Regulation of the cerebral circulation: role of endothelium and potassium channels. *Phys. Rev.,* 78:53-97.

27. Fimiani, C., Liberty, T., Aquirre, A. J., Amin, I., Ali, N., and Stefano, G. B. (1999): Opiate, cannabinoid, and eicosanoid signaling converges on common intracellular pathways: nitric oxide coupling. *Prostaglandins,* 57:23-34.

28. Fimiani, C., Mattocks, D. W., Cavani, F., Salzet, M., Deutsch, D. G., Pryor, S. C., Bilfinger, T. V., and Stefano, G. B. (1999): Morphine and anandamide stimulate intracellular calcium transients in human arterial endothelial endothelial cells: coupling to nitric oxide release. *Cellular Signaling,* 11:189-193.

29. Fricchione, G. L. and Stefano, G. B. (1994): The stress response and autoimmunoregulation. *Adv. Neuroimmunol.,* 4:13-28.

30. Holscher, C. (1997): Nitric oxide, the enigmatic neuronal messenger: its role in synaptic plasticity. *Trends Neurosci.,* 20:298-303.

31. Huang, Z., Huang, P. L., Panahian, N., Dalkara, T., Fishman, M. C., and Moskowitz, M. A. (1994): Effects of cerebral ischemia in mice deficient of neuronal nitric oxide synthase. *Science,* 265:1883-1885.

32. Huszka, M., Kaplar, M., Rejto, L., Tornai, I., Palatka, K., Laszlo, P., and Udvardy, M. (1997): The association of reduced endothelium derived relaxing factor-NO production with endothelial damage and increased in vivo platelet activation in patients with diabetes mellitus. *Thrombosis Research,* 86:173-180.

33. Iuvone, T., D'Acquisto, F., Van Osselaer, N., Di Rosa, M., Camuccio, R., and Herman, A. G. (1998): Evidence that inducible nitric oxide synthase is involved in LPS-induced plasma leakage in rat skin through the activation of nuclear factor-kappa B. *Brit. J. Pharmacol.,* 123:1325-1330.

34. Jean, A. P., Maloteaux, J. M., and Laduron, P. M. (1994): IL-1 beta-like Freund's adjuvant enhances axonal transport of opiate receptors in sensory neurons. *Neurosci. Lett.,* 177:75-78.

35. Joseph, D. B. and Bidlack, J. . M. (1994): The k-opioid receptor expressed on the mouse lymphoma cell line R1.1 contains a sulfhydryl group at the active site. *Eur. J. Pharmacol.,* 267:1-6.

36. Jun, C. D., Han, M. K., Kim, U. H., and Chung, H. T. (1996): Nitric oxide stimulates the ADP-ribosylation of actin in murine macrophages: association with the inhibition of pseudopodia formation, phagocytic activity, and adherence on a laminal substratum. *Cell. Immunol.,* 174:25-31.

37. Kinoshita, H., Tsutsui, M., Milstien, S., and Katusic, Z. S. (1997): Tetrahydrobiopterin, nitric oxide and regulation of cerebral arterial tone. *Prog. Neurobiol.,* 52:295-302.

38. Kubes, P. and Granger, D. N. (1992): Nitric oxide modulates microvascular permeability. *Am. J. Physiol.,* 262: H611-H615

39. Kubes, P., Kanwar, S., Niu, X. F., and etc. (1993): Nitric oxide synthesis inhibition induces leukocyte adhesion via superoxide and mast cells. *FASEB J.,* 7:1293-1299.

40. Kubes, P., Kurose, I., and Granger, D. N. (1994): NO donors prevent integrin-induced leukocyte adhesion but not P-selectin-dependent rolling in postischemic venules. *Am. J. Physiol.,* 267:H931-H937

41. Kubes, P., Suzuki, M. M., and Granger, D. N. (1991): Nitric oxide an endogenous modulator of leukocyte adhesion. *Proc. Natl. Acad. Sci., USA,* 88:4651-4655.

42. Kurose, I., Kubes, P., and Wolf, R. (1993): Inhibition of nitric oxide production: Mechanisms of vascular albumin leakage. *Circ. Res.,* 73:164-171.

43. Kurose, I., Wolf, R., and Granger, D. N. (1994): Dimethyl-L-arginine, an endogenous inhibitor of nitric oxide (NO) synthesis, elicits an inflammatory response in the rat mesenteric microcirculation. *Gastroenterology,* 106:A245

44. Ledebur, H. C. and Parks, T. P. (1995): Transcriptional regulation of the intercellular adhesion molecule-1 gene by inflammatory cytokines in human endothelial cells. Essential roles of a variant NF-kappa B site and p65 homodimers. *J. Biol. Chem.,* 270:933-943.

45. Liu, Y., Shenouda, D., Bilfinger, T. V., Stefano, M. L., Magazine, H. I., and Stefano, G. B. (1996): Morphine stimulates nitric oxide release from invertebrate microglia. *Brain Res.,* 722:125-131.

46. Luscinskas, F. W. and Lawler, J. (1994): Integrins as dynamic regulators of vascular function. *FASEB J.,* 8:929-939.

47. Ma, X. L., Lefer, D. A. M., and Zipkin, R. E. (1993): S-nitroso-N-acetylpenicillamine is a potent inhibitor of neutrophil-endothelial interaction. *Endothelium,* 3:32-39.

48. Mackay, F., Loetscher, H., Stueber, D., Gehr, G., and Lesslauer, W. (1993): Tumor necrosis factor alpha (TNF-alpha)-induced cell adhesion to human endothelial cells is under dominant control of one TNF receptor type, TNF-R55. *J. Exp. Med.,* 177:1277-1286.

49. Magazine, H. I. (1995): Detection of endothelial cell-derived nitric oxide: current trends and future directions. *Adv. Neuroimmunol.,* 5:479-485.

50. Magazine, H. I., Liu, Y., Bilfinger, T. V., Fricchione, G. L., and Stefano, G. B. (1996): Morphine-induced conformational changes in human monocytes, granulocytes, and endothelial cells and in invertebrate immunocytes and microglia are mediated by nitric oxide. *J. Immunol.,* 156:4845-4850.

51. Matthews, J. R., Botting, C. H., Panico, M., Morris, H. R., and Hay, R. T. (1996): Inhibition of NF-kappa B DNA binding by nitric oxide. *Nucleic Acids Res.,* 24:2236-2242.

52. McEver, R. P. (1994): *Selections Current Opinion Immunology,* 6:75-84.

53. Mohanakumar, K. P., Hanbauer, I., and Chiueh, C. C. (1998): Neuroprotection by nitric oxide against hydroxyl radical-induced nigral neurotoxicity. *J. Chem. Neuroanatomy,* 14:195-205.

54. Moncada, S. (1997): Nitric oxide in the vasculature: physiology and pathophysiology. *Annals of the New York Academy of Sciences,* 811:60-67.

55. Moncada, S. and Higgs, A. (1993): The L-arginine-nitric oxide pathway. *New Eng. J. Med.,* 329:2002-2012.

56. Moncada, S., Palmer, R. M., and Higgs, E. A. (1988): The discovery of nitric oxide as the endogenous nitrovasodilator. *Hypertension,* 12:365-372.
57. Moncada, S., Palmer, R. M. J., and Higgs, E. A. (1991): Nitric oxide: physiology, pathophysiology, and pharmacology. *Pharmacological Reviews,* 43:109-142.
58. Montgomery, K. F., Osbom, L., Hession, C., Tizard, R., Goff, D., Vassallo, C., Tarr, P. I., Bomsztyk, K., Lobb, R., and Harlan, J. M. (1991): Activation of endothelial-leukocyte adhesion molecule 1 (ELAM-1) gene transcription. *Proc. Natl. Acad. Sci., USA,* 88:6523-6527.
59. Nitenberg, A., Ledoux, S., Attali, J. R., and Valensi, P. (1997): [Response of the coronary arteries to cold test and flow velocity increase is improved by deferoxamine but not by L-arginine in diabetic patients]. [French]. *Archives des Maladies du Coeur et des Vaisseaux,* 90:1037-1041.
60. Niu, X. F., Smith, C. W., and Kubes, P. (1995): Intracellular oxidative stress induced by nitric oxide synthesis inhibition increases endothelial cell adhesion to neutrophils. *Circ. Res.,* 74:1133-1140.
61. Noiri, E., Hu, Y., Bahou, W. F., Keese, C. R., Giaever, I., and Goligorsky, M. S. (1997): Permissive role of nitric oxide in endothelin-induced migration of endothelial cells. *J. Biol. Chem.,* 272:1747-1752.
62. Noiri, E., Lee, E., Testa, J., Quigley, J., Colflesh, D., Keese, C. R., Giaever, I., and Goligorsky, M. S. (1998): Podokinesis in endothelial cell migration: role of nitric oxide. *Am. J. Physiol.,* 274:C236-C244
63. Noiri, E., Peresleni, T., Srivastava, N., Weber, P., Bahou, W. F., Peunova, N., and Goligorsky, M. S. (1998): Nitric oxide is necessary for a switch from stationary to locomoting phenotype in epithelial cells. *Am. J. Physiol.,* 270: C794-C802
64. Ottaviani, E., Paemen, L. R., Cadet, P., and Stefano, G. B. (1993): Evidence for nitric oxide production and utilization as a bacteriocidal agent by invertebrate immunocytes. *Eur. J. Pharmacol.,* 248:319-324.
65. Peng, H. B., Libby, P., and Liao, J. K. (1995): Induction and stabilization of I kappa B alpha by nitric oxide mediates inhibition of NF-kappa B. *J. Biol. Chem.,* 270:14214-14219.
66. Peunova, N. and Enikolopov, G. (1993): Amplification of calcium-induced gene transcription by nitric oxide in neuronal cells. *Nature,* 364:453
67. Peunova, N. and Enikolopov, G. (1995): Nitric oxide triggers a switch to graowth arrest during differentiation of neuronal cells. *Nature,* 375:68-73.
68. Pitei, D. L., Watkins, P. J., and Edmonds, M. E. (1997): NO-dependent smooth muscle vasodilatation is reduced in NIDDM patients with peripheral sensory neuropathy. *Diabetic Medicine,* 14:284-290.
69. Pober, J. S. and Cotran, R. S. (1990): Cytokines and endothelial cell biology. *Physiol. Rev.,* 70:427-451.
70. Prevot, V., Croix, D., Rialas, C. M., Puolain, P., Frichione, G. L., Stefano, G. B., and Beauvillain, J. C. (1999): Estradiol coupling to endothelial nitric oxide production stimulates GnRH release from rat median eminence. *Endocrinol.,* 140:652-659.
71. Prevot, V., Rialas, C., Croix, D., Salzet, M., Dupouy, J.-P., Puolain, P., Beauvillain, J. C., and Stefano, G. B. (1998): Morphine and anandamide coupling to nitric oxide stimulated GnRH and CRF release from rat median eminence: neurovascular regulation. *Brain Res.,* 790:236-244.
72. Radomski, M. W., Palmer, R. M. J., and Moncada, S. (1987): Endogenous nitric oxide inhibits human platelet adhesion to vascular endothelium. *Lancet,* 2:1057-1058.
73. Radomski, M. W., Palmer, R. M. J., and Moncada, S. (1990): Glucocorticoids inhibit the expression of an inducible, but not the consitutive, nitric oxide synthase in vascular endothelial cells. *Proc. Natl. Acad. Sci., USA,* 87:10043-10047.
74. Read, M. A., Whitley, M. Z., Williams, A. J., and Collins, T. (1994): NF-kappa B and I kappa B alpha: an inducible regulatory system in endothelial activation. *J. Exp. Med.,* 179:503-512.
75. Roebuck, K. A., Rahman, A., Lakshminarayanan, V., Janakidevi, K., and Malik, A. B. (1995): H2O2 and tumor necrosis factor-alpha activate intercellular adhesion molecule 1 (ICAM-1) gene transcription through distinct cis-regulatory elements within the ICAM-1 promoter. *J. Biol. Chem.,* 270:18966-18974.
76. Salzet, M., Cocquerelle, C., Verger-Bocquet, M., Pryor, S. C., Rialas, C. M., Laurent, V., and Stefano, G. B. (1997): Leech immunocytes contain proopiomelanocortin: nitric oxide mediates hemolymph POMC processing. *J. Immunol.,* 159:5400-5411.
77. Salzet, M. and Stefano, G. B. (1997): Invertebrate proenkephalin: Delta opioid binding sites in leech ganglia and immunocytes. *Brain Res.,* 768:232
78. Scharrer, B. and Stefano, G. B. (1994): Neuropeptides and autoregulatory immune processes. In: *Neuropeptides and immunoregulation,* edited by B. Scharrer, et al, pp. 1-18. Springer-Verlag,
79. Sekkai, D., Aillet, F., Israel, N., and Lepoivre, M. (1998): Inhibition of NF-kappaB and HIV-1 long terminal repeat transcriptional activation by inducible nitric oxide synthase 2 activity. *J. Biol. Chem.,* 273:3895-3900.
80. Shin, W. S., Hong, Y. H., Peng, H. B., DeCaterina, R., Libby, P., and Liao, J. K. (1996): Nitric oxide attenuates vascular smooth muscle cell activation by interferon-gamma. The role of constitutive NF-kappa B activity. *J. Biol. Chem.,* 71:11317-11324.
81. Siebenlist, U., Franzoso, G., and Brown, K. (1994): Structure, regulation and function of NF-kappa B. *Ann. Rev. Cell. Biol.,* 10:405-455.
82. Simon, D. I., Stamler, J. S., Jaraki, O., and etc. (1993): Antiplatelet properties of protein S-nitrosothiols derived from nitric oxide and endothelium-derived relaxing factor. *Arterioscler. Thromb.,* 13:791-799.
83. Sonetti, D., Ottaviani, E., Bianchi, F., Rodriquez, M., Stefano, M. L., Scharrer, B., and Stefano, G. B. (1994): Microglia in invertebrate ganglia. *Proc. Natl. Acad. Sci. USA,* 91:9180-9184.
84. Sonetti, D., Ottaviani, E., and Stefano, G. B. (1997): Opiate signaling regulates microglia activities in the invertebrate nervous system. *Gen. Pharmacol.,* 29:39-47.
85. Spiecker, M., Darius, H., Kaboth, K., Hubner, F., and Liao, J. K. (1998): Differential regulation of endothelial cell adhesion molecule expression by nitric oxide donors and antioxidants. *J. Leukocyte Biol.,* 63:732-739.
86. Spiecker, M., Peng, H. B., and Liao, J. K. (1997): Inhibition of endothelial vascular cell adhesion molecule-1 expression by nitric oxide involves the induction and nuclear translocation of I kappa B alpha. *J. Biol. Chem.,* 272:30969-30974.
87. Springer, T. A. (1994): Traffic signals for lymphocyte recirculation and leukocyte emigration. *Cell,* 67:301-314.
88. Stefano, G. B. (1989): Role of opioid neuropeptides in immunoregulation. *Prog. Neurobiol.,* 33:149-159.
89. Stefano, G. B. (1992): Invertebrate and vertebrate immune and nervous system signal molecule commonalities. *Cell. Mol. Neurobiol.,* 12:357-366.

90. Stefano, G. B. (1998): Autoimmunovascular regulation: morphine and anandamide stimulated nitric oxide release. *Journal of Neuroimmunology*, 83:70-76.
91. Stefano, G. B., Bilfinger, T. V., and Fricchione, G. L. (1994): The immune neuro-link and the macrophage: Post-cardiotomy delirium, HIV-associated dementia and psychiatry. *Prog. Neurobiol.*, 42:475-488.
92. Stefano, G. B., Cadet, P., and Scharrer, B. (1989): Stimulatory effects of opioid neuropeptides on locomotory activity and conformational changes in invertebrate and human immunocytes: Evidence for a subtype of delta receptor. *Proc. Natl. Acad. Sci. USA*, 86:6307-6311.
93. Stefano, G. B., Christensen, V. B., Tonnesen, E., Liu, Y., Hughes, T. K., and Bilfinger, T. V. (1997): Interleukin 10 stimulation of endogenous nitric oxide release from human saphenous veins diminishes immunocyte adherence. *J. Cardiovasc. Pharmacol*, 30:90-95.
94. Stefano, G. B., Hartman, A., Bilfinger, T. V., Magazine, H. I., Liu, Y., Casares, F., and Goligorsky, M. S. (1995): Presence of the mu3 opiate receptor in endothelial cells: Coupling to nitric oxide production and vasodilation. *J. Biol. Chem.*, 270:30290-30293.
95. Stefano, G. B., Leung, M. K., Zhao, X., and Scharrer, B. (1989): Evidence for the involvement of opioid neuropeptides in the adherence and migration of immunocompetent invertebrate hemocytes. *Proc. Natl. Acad. Sci. USA*, 86:626-630.
96. Stefano, G. B., Liu, Y., and Goligorsky, M. S. (1996): Cannabinoid receptors are coupled to nitric oxide release in invertebrate immunocytes, microglia, and human monocytes. *J. Bio. Chem.*, 271:19238-19242.
97. Stefano, G. B., Liu, Y., and Scharrer, B. (1996): A focused review of novel immunocyte opioid and opiate receptors. *Chinese J. Immunol.*, (in press)
98. Stefano, G. B., Melchiorri, P., Negri, L., Hughes, T. K., and Scharrer, B. (1992): (D-Ala2)-Deltorphin I binding and pharmacological evidence for a special subtype of delta opioid receptor on human and invertebrate immune cells. *Proc. Natl. Acad. Sci. USA*, 89:9316-9320.
99. Stefano, G. B., Prevot, V., Beauvillain, J. C., Bilfinger, T. V., Fimiani, C., Welters, I., and Fricchione, G. L. (2000): Acute exposure of estrogen to human endothelia results in nitric oxide release mediated by an estrogen surface receptor coupled to intracellular calcium transients. *Circulation*, 101:1594-1597.
100. Stefano, G. B., Salzet-Raveillon, B., and Salzet, M. (1998): *Mytilus edulis* hemocytes contains pro-opiomelanocortin: LPS and morphine stimulate differential processing. *Mol. Brain Res.*, 63:340-350.
101. Stefano, G. B., Salzet, B., and Fricchione, G. L. (1998): Enkelytin and opioid peptide association in invertebrates and vertebrates: immune activation and pain. *Immunol. Today*, 19:265-268.
102. Stefano, G. B., Salzet, B., Rialas, C. M., Pope, M., Kustka, A., Neenan, K., Pryor, S. C., and Salzet, M. (1997): Morphine and anandamide stimulated nitric oxide production inhibits presynaptic dopamine release. *Brain Res.*, 763:63-68.
103. Stefano, G. B. and Salzet, M. (1999): Invertebrate opioid precursors: evolutionary conservation and the significance of enzymatic processing. *Int. Rev. Cytol.*, 187:261-286.
104. Stefano, G. B., Salzet, M., and Bilfinger, T. V. (1998): Long-term exposure of human blood vessels to HIV gp120, morphine and anandamide increases endothelial adhesion of monocytes: Uncoupling of Nitric Oxide. *J. Cardiovasc. Pharmacol*, 31:862-868.
105. Stefano, G. B., Salzet, M., Magazine, H. I., and Bilfinger, T. V. (1998): Antagonist of LPS and IFN- induction of iNOS in human saphenous vein endothelium by morphine and anandamide by nitric oxide inhibition of adenylate cyclase. *J. Cardiovasc. Pharmacol*, 31:813-820.
106. Stefano, G. B., Salzet, M., Rialas, C., Mattocks, D. W., Fimiani, C., and Bilfinger, T. V. (1998): Macrophage behavior associated with acute and chronic exposure to HIV GP120, morphine and anandamide: endothelial implications. *Int. J. Cardiol.*, 64:S3-S 13
107. Stefano, G. B. and Scharrer, B. (1994): Endogenous morphine and related opiates, a new class of chemical messengers. *Adv. Neuroimmunol.*, 4:57-68.
108. Stefano, G. B. and Scharrer, B. (1996): The presence of the 3 opiate receptor in invertebrate neural tissues. *Comp. Biochem. Physiol.*, 113C:369-373.
109. Stefano, G. B., Scharrer, B., Smith, E. M., Hughes, T. K., Magazine, H. I., Bilfinger, T. V., Hartman, A., Fricchione, G. L., Liu, Y., and Makman, M. H. (1996): Opioid and opiate immunoregulatory processes. *Crit. Rev. in Immunol.*, 16:109-144.
110. Suematsu, M., Tamatani, T., Delano, F. A., Miyasaka, M., Forrest, M., Suzuki, H., and Schmid-Schonbein, G. W. (1994): Microvascular oxidative stress preceding leukocyte activation elicited by in vivo nitric oxide suppression. *Am. J. Physiol.*, 266:H2410-H2415
111. Szabo, C. (1996): Physiological and pathophysiological roles of nitric oxide in the central nervous system. *Brain Res. Bull.*, 41:131-141.
112. Togashi, H., Sasaki, M., Frohman, E., Taira, E., Ratan, R. R., Dawson, T. M., and Dawson, V. L. (1997): Neuronal (type 1) nitric oxide synthase regulates nuclear factor kappa B activity and immunologic (type II) nitric oxide synthase expression. *Proc. Natl. Acad. Sci., USA*, 94:2676-2680.
113. Turner, A., Leung, M. K., and Stefano, G. B. (1994): Peptidases of significance in neuroimmunoregulation. In: *Neuropeptides in neuroimmunology*, edited by B. Scharrer, et al, pp. 152-169. Springer-Verlag,
114. Welters, I., Fimiani, C., Bilfinger, T. V., and Stefano, G. B. (1999): NF-kB, nitric oxide and opiate signaling. *Medical Hypotheses*, 54:263-268.
115. Wink, D., Hanbauer, I., Krishna, M. C., DeGraff, W., Gamson, J., and Mitchell, J. B. (1993): Nitric oxide protects against cellular damage and cytotoxicity from reactive oxygen species. *Proc. Natl. Acad. Sci., USA*, 90:9813-9817.
116. Xie, Q. and Nathan, C. (1994): The high-output nitric oxide pathway: role and regulation. *J. Leukocyte Biol.*, 56:576-582.
117. Bilfinger, T. V. et al. "Pharmacological evidence for anandamide amidase in human cardiac and vascular tissues." *Int. J. Cardiol.* 64.1 (1998): S15-S22.
118. Bilfinger, T. V. et al. "Direct assessment of diminished production of morphine stimulated NO by diabetic endothelium from saphenous vein." *Acta Pharmacologica Sinica* 23.2 (2002): 97-102.
119. Deutsch, D. G et al. "Production and physiological actions of anandamide in the vasculature of the rat kidney." *Journal of Clinical Investigation* 100 (1997): 1538-46.

What is claimed is:

1. A pharmaceutical composition for stimulating nitric oxide production in mammalian cells, said pharmaceutical composition comprising an effective amount of extract of

*Salix alba*, wherein the *Salix alba* extract is prepared by a process comprising:
 (a) homogenizing dried *Salix alba* in an acidic solution;
 (b) preparing a supernatant by separating solid material from the homogenized acidic solution using alcohol extraction and centrifugal filtration;
 (c) drying the supernatant;
 (d) preparing an elute by dissolving the supernatant in an aqueous solution containing trifluroacetic acid and extracting a solid phase; and
 (e) purifying the elute using high performance liquid chromatography to obtain said extract.

2. The pharmaceutical composition according to claim 1, the process further comprising:
 identifying and characterizing the extract using mass spectrometric analysis.

3. The pharmaceutical composition according to claim 1, wherein the extract stimulates nitric oxide production in mammalian cells.

4. The pharmaceutical composition according to claim 1, wherein the extract contains a first compound with a molecular weight of 263.3 Daltons and a second compound with a molecular weight of 356.5 Daltons and a third compound with a molecular weight of 337.5 Daltons and a fourth compound with a molecular weight of 354.4 Daltons.

5. The pharmaceutical composition according to claim 1, wherein the composition has at least one component selected from a group consisting of: a component have a molecular weight of 353.28 Daltons, a component have a molecular weight of 109.09 Daltons, and a component have a molecular weight of 97.1 Daltons.

6. The pharmaceutical composition according to claim 1, wherein the composition has the ability to stimulate nitric oxide release in the range of 15 nM to 100 nM in pedal ganglia cells.

7. The pharmaceutical composition according to claim 1, wherein the composition has the ability to stimulate nitric oxide release in the range of 50 nM to 100 nM in endothelial cells.

8. The pharmaceutical composition according to claim 1, wherein said extract displays a single major peak on high performance liquid chromatographic analysis in 10 nM sodium chloride, 0.5 mM EDTA, 100 mM sodium acetate and 50% acetonitrile, pH 5.0.

9. A method of preparing a *Salix alba* extract, comprising:
 homogenizing dried *Salix alba* in an acidic solution;
 preparing a supernatant by separating solid material from the homogenized acidic solution using alcohol extraction and centrifugal filtration;
 drying the supernatant;
 preparing an elute by dissolving the supernatant in an aqueous solution containing trifluroacetic acid and extracting a solid phase; and
 purifying the elute using high performance liquid chromatography to obtain said extract.

10. The method according to claim 9, further comprising:
 identifying and characterizing the extract using mass spectrometric analysis.

11. The method according to claim 9, wherein the extract stimulates nitric oxide production in mammalian cells.

12. The method according to claim 9, wherein the extract contains a first compound with a molecular weight of 263.3 Daltons and a second compound with a molecular weight of 356.5 Daltons and a third compound with a molecular weight of 337.5 Daltons and a fourth compound with a molecular weight of 354.4 Daltons.

13. The method according to claim 9, wherein the extract includes at least one component selected from a group consisting of: a component have a molecular weight of 353.28 Daltons, a component have a molecular weight of 109.09 Daltons, and a component have a molecular weight of 97.1 Daltons.

* * * * *